United States Patent [19]

Kondo et al.

[11] 4,238,396

[45] Dec. 9, 1980

[54] 1-HYDROCARBYL-PYRROLE-2-ACETIC ACID DERIVATIVES AND THEIR PRODUCTION

[75] Inventors: Kiyosi Kondo, Yamato; Minoru Suda; Daiei Tunemoto, both of Sagamihara, all of Japan

[73] Assignee: Sagami Chemical Research Center, Japan

[21] Appl. No.: 963,673

[22] Filed: Nov. 27, 1978

[30] Foreign Application Priority Data

Dec. 8, 1977 [JP] Japan .................................. 52/146581
Dec. 8, 1977 [JP] Japan .................................. 52/146582

[51] Int. Cl.$^3$ ............................................. C07D 207/34
[52] U.S. Cl. ............................ 260/326.2; 260/326.47; 260/326.5 R; 260/326.62
[58] Field of Search ............ 260/326.2, 326.47, 326.62, 260/326.5 R

[56] References Cited

U.S. PATENT DOCUMENTS

| | | | |
|---|---|---|---|
| 3,752,826 | 8/1973 | Carson | 260/326.2 |
| 3,755,307 | 8/1973 | Carson | 260/376.47 |
| 3,803,171 | 4/1974 | Carson | 260/326.47 |

OTHER PUBLICATIONS

Entemann et al., J.A.C.S., vol. 55, pp. 2900–2903, (1933).
Ivanoff et al., *Bulletin de la Societe Chemique de France*, vol. 49, pp. 371–395 (1931).
*Comptes Rendus*, vol. 192, pp. 363–365, (1931).
Fischer et al., "Die Chemie des Pyrrols", pp. 209–212, (1943), pp. 260–265 (1943).
Blenn et al., J.A.C.S., vol. 76, pp. 37–39 (1954).
Kharasch et al., "Grignard Reactions of Nonmetallic Substances", pp. 767–845 (1954).
Carson et al., J. Org. Chem., vol. 42, pp. 1096–1098, (1977).
Müller, Methoden der Organischen Chemie, vol. 7/2a, p. 616 (1973).
Kharasch et al., "Grignard Reactions of Non-metallic Substances", pp. 948–960 (1954).

*Primary Examiner*—Mary C. Lee

[57] ABSTRACT

5-Cyano-1-hydrocarbylpyrrole-2-acetic acid is converted to 5-acyl-1-hydrocarbylpyrrole-2-acetic acid by reaction with a Grignard reagent followed by hydrolysis. The cyano compound, novel per se, is produced by reacting 1-hydrocarbyl-2-(2',2',2'-trihalo-1'-hydroxyethyl)pyrrole with a cyanating reagent under basic conditions. The latter pyrrole is in turn formed by reacting 1-hydrocarbylpyrrole with trihaloacetaldehyde such as chloral, preferably in the presence of added organic acid catalyst.

21 Claims, No Drawings

1-HYDROCARBYL-PYRROLE-2-ACETIC ACID DERIVATIVES AND THEIR PRODUCTION

This invention relates to 5-cyano-1-hydrocarbylpyrrole-2-acetic acid, its preparation and its use as a precursor for producing 5-acyl-1-hydrocarbylpyrrole-2-acetic acids.

A wide variety of 5-acyl-1-hydrocarbylpyrrole-2-acetic acids are known to possess useful pharmacological properties. For example, 1-methyl-5-p-toluoylpyrrole-2-acetic acid has a marked anti-inflammatory activity [J. Pharmacology and Experimental Therapeutics, 185, 127 (1973)]. See also U.S. Pat. Nos. 3,752,826; 3,755,307; 3,803,169; 3,803,171 and 4,048,191 which describe, inter alia, numerous 5-acyl-1-hydrocarbylpyrrole-2-acetic acids having anti-inflammatory and analgetic activities.

Conventionally, 5-acylpyrrole-2-acetic acids such as 1-methyl-5-aroylpyrrole-2-acetic acids are prepared by acylation of the corresponding pyrrole-2-acetic acid, pyrrole-2-acetic acid ester, or pyrrole-2-acetonitrile. Known methods for preparing the starting pyrrole-2-acetic acid derivatives used in these acylation processes include the following:

(1) A method for obtaining 1-methylpyrrole-2-acetic acid esters by reacting 1-methylpyrrole with ethyl diazoacetate in the presence of copper powder as a catalyst [J. Org. Chem., 14, 664 (1946)].

(2) A method for preparing 1-methylpyrrole-2-acetic acid by treating the product, which is obtained by Friedel-Crafts reaction of 1-methylpyrrole and oxalyl chloride, with alcohols to synthesize (1-methylpyrrolyl)glyoxalic acid ester, and reacting it with hydrazine, followed by treating with potassium hydroxide [Wolff-Kishner reaction] [Liebigs Ann. Chem., 721, 105 (1969)].

(3) A method for obtaining 1-methylpyrrole-2-acetic acid by hydrolysis of 1-methylpyrrole-2-acetonitrile, which in turn is prepared by reacting 1-methylpyrrole with dimethylamine and formaldehyde to afford a so-called Mannich base (Mannich reaction), and changing it into methiodide by the reaction with methyl iodide, followed by reacting with sodium cyanide [J. Amer. Chem. Soc., 73, 4921 (1951)].

These methods have some defects in that the yields tend to be low and in that in many cases use is made of starting materials or reagents which are difficult to obtain in industrial-scale quantities.

Among the methods for acylation of the appropriate pyrrole-2-acetic acid derivative, the following are known:

(1) Reacting the pyrrole-2-acetic acid derivative with aroyl chloride in the presence of alkyl aluminum chloride [Ger. Offen. No. 2,524,299].

(2) Acylation using the mixed acid anhydrides obtained form aryl carboxylic acid and trifluoroacetic anhydride [Japan Patent Publication 46-418].

(3) Acylation using the reaction product obtained from N,N-dimethyl aroyl amide and phosphoryl chloride [Japan Patent Publication No. 46-418].

(4) Acylation using the mixed anhydrides obtained from aryl carboxylic anhydride and methane sulfonic acid and the like [Japan Patent Publication No. 50-126660].

(5) Reacting the pyrrole-2-acetic acid derivative with phosgene to afford 5-chlorocarbonyl derivatives and then reacting them with aryl metallic compounds. [U.S. Pat. No. 3,846,447].

(6) Uncatalyzed aroylation of 1-alkylpyrrole-2-acetic acid derivatives with aroyl chloride using an aprotic solvent [U.S. Pat. No. 3,998,844].

(7) Acylation of the appropriate pyrrole-2-acetic acid derivative with various acylating agents in the presence of a Lewis acid such as aluminum chloride [U.S. Pat. No. 3,752,826; 3,755,307; 3,803,169; 3,803,171].

These methods have some defects such as their low yields or the necessity of separating by-produced isomer having an acyl group at the 4-position.

The present inventors have established a process for preparing 5-acyl-1-hydrocarbylpyrrole-2-acetic acids in high yields, by use of 5-cyano-1-hydrocarbylpyrrole-2-acetic acid, preferably 5-cyano-1-methylpyrrole-2-acetic acid, as a starting material which can easily be obtained in industrial scale. In this process the 5-cyano-1-hydrocarbylpyrrole-2-acetic acid is reacted with a Grignard compound and the resultant reaction product is hydrolyzed.

5-Cyano-1-methylpyrrole-2-acetic acid, the preferred starting material in this process, can easily be prepared by reacting 1-methyl-2-(2',2',2'-trihalo-1'-hydroxyethyl)pyrrole, which is formed by the reaction of 1-methylpyrrole and trihaloacetaldehyde, with a cyanating reagent under basic conditions. Substitution of other 1-hydrocarbylpyrroles, such as 1-ethylpyrrole, 1-propylpyrrole, 1-amylpyrrole, 1-phenylpyrrole, 1-cyclohexylpyrrole, 1-benzylpyrrole and 1,3-dimethylpyrrole, in this reaction sequence gives other 5-cyano-1-hydrocarbylpyrrole-2-acetic acids of this invention.

Grignard compounds, the other starting material in this process, can also easily be prepared from the corresponding organic halide by applying the general Grignard synthesis. Methods for producing a wide variety of Grignard compounds are well documented in the literature—see for example Kharasch and Reinmuth, "Grignard Reaction of Nonmetallic Substances," Prentice-Hall, New York, 1954; and "Metal-Organic Compounds," (Number 23 of the Advances in Chemistry Series), American Chemical Society, Washington, D.C., 1959, pages 73–81.

ACYLATION PROCESS

In carrying out the acylation process of this invention, the use of solvents is preferred and examples of the solvent used are ethers such as ether, dioxane, THF, dimethoxyethane and the like, or hydrocarbons containing organic tertiary amines. In these solvents, Grignard reagent is prepared and then the 5-cyano-1-hydrocarbylpyrrole-2-acetic acid is added. The reaction can preferably be carried out at room temperature or at a reflux temperature of the solvent used. In this reaction, preferably the Grignard reagent is used in an amount of more than two molar equivalents. One molar equivalent of Grignard reagent is consumed for the production of carboxylic acid salt and the balance is used for the introduction of the acyl group.

The reaction mixture formed in this step is worked-up and then hydrolyzed. The hydrolysis can be accomplished by the direct addition of acidic substances such as hydrochloric acid, sulfuric acid, phosphoric acid, oxalic acid, aqueous ammonium chloride and the like. From the standpoint of the reaction mechanism, the reaction would proceed via the formation of a ketimine salt as an intermediate as follows:

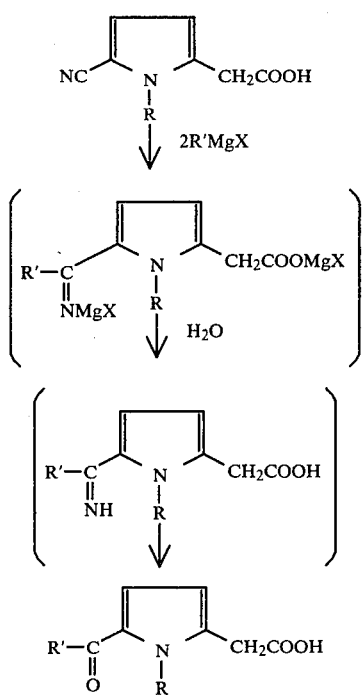

(wherein R and R' represent organic groups such as alkyl, aryl and the like, and X represents a halogen atom).

The compound of the formula (I) in this invention can be prepared as follows:

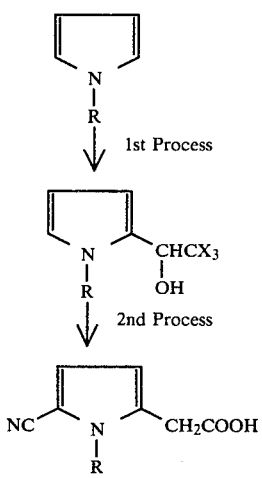

(wherein X represents a halogen atom and R represents a hydrocarbon group, preferably lower alkyl and most preferably, methyl). Innocuous substituents (alkyl, etc.) can be present in the 3- and/or 4-positions of the ring.

1ST PROCESS—ADDUCT FORMATION

In the first process of this invention, it is essential to react the pyrrole reactant with trihaloacetaldehyde to produce the adduct (II). 1-Methyl-2-(2',2',2'-trihalo-1'-hydroxyethyl)pyrrole (Formula (II); R=methyl) obtained using 1-methylpyrrole in this process is a known compound, and as to its synthetic method, it has been reported that 1-methylpyrrole is reacted with freshly distilled chloral in the presence of molecular quantities of zinc chloride, a Lewis acid [R. C. Blinn et al., J. Amer. Chem. Soc., 76, 37 (1954)]. However, it is difficult to use this process in industrial scale because the yield is very low such as only 26.5%. As a result of further studies on this process, the present inventors have found that it is possible to obtain the compound of the formula (II) in almost quantitative yield, by treating the reactants at from −10° C. to room temperature, without using added catalysts such as Lewis acid and the like. It was discovered that the rate of this reaction—which is preferably conducted in the presence of solvents which do not directly affect on the reaction, for example, ethereal solvents such as diethyl ether, dioxane, THF, and the like, and hydrocarbons such as benzene, toluene, hexane, and the like—is dependent on the origin (or the purity) of chloral used. Chloral from a freshly opened bottle did not react with N-methylpyrrole at room temperature and only after prolonged reflux (sometimes several days) was the adduct formed. In contrast, chloral from an old bottle reacted instantly at room temperature. Acting on the hypothesis that trichloroacetic acid, which is formed easily by the oxidation of chloral, does catalyze this reaction, the present inventors have found that the addition of organic acid such as trichloroacetic acid, acetic acid or p-toluenesulfonic acid to the reaction mixture accelerates this reaction. Among these three acids, p-toluene-sulfonic acid presently appears even more effective than the others. By conducting the process in the presence of a protonic acid added preferably in the form of either an organic acid or a cation exchange resin (e.g., Amberlyst), the adduct has been readily formed in almost quantitative yield.

2ND PROCESS—CYANATION/BASIC HYDROLYSIS

In this process, it is essential to react the compound of the Formula (II) with a cyanating reagent under basic conditions. Examples of cyanating reagent are inorganic cyanides such as potassium cyanide, sodium cyanide, cuprous cyanide, and the like, and acetone cyanohydrin and the like. Establishment of the basic conditions can be achieved by using a large amount of the cyanating reagent when it is a base. More preferably, the cyanation is performed in the presence of alkali metal salts such as sodium carbonate, potassium carbonate and the like; alkali metal hydroxides such as sodium hydroxide, potassium hydroxide and the like; or alkali metal alkoxides such as sodium methoxide, sodium ethoxide, potassium methoxide, and the like (in this case, the presence of water is essential). Use of sodium hydroxide or potassium hydroxide is most preferred.

In carrying out this reaction, the use of solvents is preferred and examples of the solvent used are alcohols such as methanol and ethanol, ethers such as ether, dioxane, THF, and like polar solvents such as dimethylformamide, dimethyl sulfoxide, and sulfolane, and their mixed solvent with water. Thus far, the best results have been obtained using a mixture of methanol and water as the reaction solvent. The reaction proceeds at or under room temperature, and, if necessary, the reaction mixture can be heated.

Under the above-mentioned conditions and by separating the acidic portion from the resulting reaction mixture, for example, by extraction with alkali and subsequent acidification, the desired 5-cyano-1-hydrocarbylpyrrole-2acetic acid can selectively be obtained.

The present invention is further illustrated in detail by the following Examples.

EXAMPLE 1—ADDUCT FORMATION—NO CATALYST ADDED

To a solution of N-methylpyrrole (810 mg, 10 mmol) dissolved in benzene (10ml) was added dropwise a solution of chloral (1.47 g, 10 mmol) dissolved in benzene (5 ml) under ice-cooling for 40 minutes. After the mixture was stirred for 1 hour at room temperature, water was added thereto and the mixture was extracted with ether. The extract was dried over sodium sulfate and concentrated to afford 1-methyl-2-(2',2',2'-trichloro-1'-hydroxyethyl)pyrrole (2.04 g) as an oil.

Yield: 90%

NMR (CCl$_4$): δ3.61 (3H,s), 5.03 (1H,s), 5.95 (1H,m), 6.32 (1H,m), 6.47 (1H,m).

EXAMPLE 2—ADDUCT FORMATION—ACID CATALYST ADDED

To a solution of N-methylpyrrole (8.10 g, 0.1 mol) in ether (50 ml) was added a solution of chloral (16.21 g, 0.1 mol) in ether (50 ml). To this were added p-toluenesulfonic acid (200 mg) and hydroquinone (5 mg). Then the mixture was refluxed for 15 hours. After adding triethylamine (5 ml), the mixture was stirred for 5 minutes. Brine (100 ml) was added and the organic layer separated. The aqueous layer was extracted with ethyl acetate, and the combined organic layers were washed with brine (100 ml). After drying over magnesium sulfate, the organic solution was filtered through a bed of activated charcoal, and concentration afforded the adduct 1-methyl-2-(2',2',2'-trichloro-1'-hydroxyethyl)pyrrole (24.1 g) as pale brown prisms.

EXAMPLE 3—ADDUCT FORMATION AND CYANATION/BASIC HYDROLYSIS

N-Methylpyrrole (2.43 g, 30.0 mmol) and chloral (4.50 g, 30.5 mmol) were reacted in dioxane (10 ml) at room temperature for 4 hours to afford the above adduct. This solution was added dropwise to a solution of potassium cyanide (1.90 g, 47.5 mmol) dissolved in methanol (100 ml). Potassium carbonate (8 g, 58 mmol) was added and the mixture was stirred at room temperature for 5 days. After removal of most of the solvent, water was added and the mixture was washed with methylene chloride. The layer of methylene chloride was dried and then concentrated to afford the starting adduct (7.2 mmol) and 1-methylpyrrole-2-aldehyde (2.6 mmol). The aqueous layer was made acidic with HCl and extracted with methylene chloride. The extract was dried over MgSO$_4$ and concentrated. The residue was purified by column chromatography to afford 5-cyano-1-methylpyrrole-2-acetic acid (940 mg).

Yield: 25% m.p. 125°–126° C.

NMR (CDCl$_3$): δ3.64 (5H,s), 6.05 (1H,d,J=4 Hz), 6.68 (1H,d,J=4 Hz).

IR (KBr): 3200, 2215, 1740 cm$^{-1}$.

EXAMPLE 4—ADDUCT FORMATION AND CYANATION/BASIC HYDROLYSIS

N-Methylpyrrole (1.62 g, 20.0 mmol) and chloral (3.20 g, 21.7 mmol) were reacted in dioxane (5 ml) to afford the adduct. A solution of potassium cyanide (5.70 g, 88 mmol) and potassium carbonate (2.80 g, 20 mmol) dissolved in methanol (150 ml) was added to the adduct and the mixture was stirred for 4 days. Then sodium hydroxide (3.0 g, 75 mmol) was added portion-wise to the mixture for the next 3 days. The reaction mixture was worked-up in the same manner as described in Example 3 above to afford the desired product, 5-cyano-1-methylpyrrole-2-acetic acid (1.50 g).

Yield: 50%

EXAMPLE 5—ADDUCT FORMATION AND CYANATION/BASIC HYDROLYSIS

N-Methylpyrrole (1.62 g, 20.0 mmol) and chloral (3.20 g, 21.7 mmol) were reacted in dioxane (5 ml) to afford the adduct. A solution of potassium cyanide (6.20 g, 95 mmol) and potassium carbonate (2.80 g) dissolved in methanol (100 ml) was added to the solution and the mixture was heated under reflux for 21 hours. The reaction mixture was worked-up in the same manner as described in Example 3 above to afford the same product (880 mg).

Yield: 27%

EXAMPLE 6—ADDUCT FORMATION AND CYANATION/BASIC HYDROLYSIS

An ether (10 ml) solution of N-methylpyrrole (810 mg, 10 mmol) and chloral (1.6 g, 10.7 mmol) was refluxed for 24 hours. The solvent was removed at room temperature under vacuum and the residue was dissolved in methanol (30 ml). This solution was added to a solution of sodium cyanide (3.0 g, 60 mmol) in water (30 ml). To this solution, heated to 30°–35° C. in an oil bath, was added during 20 hours a solution of potassium hydroxide (2.6 g, 40 mmol) in water (15 ml). After completion of the addition, the mixture was kept at the same temperature for 2 additional hours. The mixture was then diluted with water and washed with methylene chloride (this organic layer contains almost no starting material). The aqueous layer was acidified carefully using hydrochloric acid and extracted with methylene chloride several times. The extracts were combined and washed with brine. After drying over magnesium sulfate, the organic solution was concentrated. The residue was chromatographed on silica-gel(hexane-ethyl acetate eluent) to give the desired cyano acid, 5-cyano-1-methylpyrrole-2-acetic acid (945 mg), the yield being 58%.

EXAMPLE 7—CYANATION/BASIC HYDROLYSIS

The chloral/N-methylpyrrole adduct prepared as in Example 6 was cyanated using variations of the general procedure of Example 6. The reaction conditions used and results obtained are summarized in the Table.

TABLE

Production of 5-Cyano-1-Methylpyrrole-2-Acetic Acid

| Run | Base | Solvent | Temp(°C.) | Yield |
|---|---|---|---|---|
| 1 | K$_2$CO$_3$ | DMSO—H$_2$O | 40 | 37 |
| 2 | KOH | DMSO—H$_2$O | r.t. | 41 |
| 3 | K$_2$CO$_3$ | DMSO—H$_2$O | 40–45 | 45 |
| 4 | KOH | MeOH—H$_2$O | r.t. | 46 |
| 5 | KOH | MeOH—H$_2$O | 35 | 55 |

EXAMPLE 8—ACYLATION

A Grignard reagent was prepared from magnesium (1.14 g, 46.9 m atom) and p-bromotoluene (8.20 g, 47.9 mmol) in THF. A solution of 5-cyano-1-methylpyrrole-2-acetic acid (1.61 g, 9.8 mmol) dissolved in THF (5 ml) was added to the above solution and the mixture was heated under reflux for 2 hours. After acidifying with HCl, the mixture was extracted with ether. The ether layer was dried, concentrated, and then purified by silica-gel column chromatography to afford 500 mg of the starting nitrile. The aqueous layer was allowed to stand at room temperature for 2 weeks. This reaction mixture was then extracted with ether, and the ethereal layer was dried and concentrated to give crystals of 1-methyl-5-p-toluoylpyrrole-2-acetic acid (1.60 g).

Yield: 92% m.p. 155°–156° C.

NMR (CDCl$_3$): δ2.37 (3H,s), 3.69 (2H,s), 3.89 (3H,s), 6.06 (1H,d,J=4 Hz), 6.62 (1H,d,J=4 Hz), 7.18 (2H,d,J=8 Hz), 7.66 (2H,d,J=8 Hz).

IR (KBr): 3425, 2940, 2900, 1700, 1600 cm$^{-1}$.

EXAMPLE 9—ACYLATION

In the same manner as described in Example 8, Grignard reagent was prepared from magnesium (890 mg, 36.6 m atom) and p-bromotoluene (6.25 g, 36.5 mmol). To this solution was added a solution of 5-cyano-1-methylpyrrole-2-acetic acid (1.50 g, 9.14 mmol) dissolved in THF (15 ml) and the mixture was heated under reflux for 21 hours. After addition to the mixture of ether saturated with water, acetic acid (4 ml) and water were added thereto. The aqueous layer was washed with methylene chloride and dioxane (100 ml) and concentrated HCl (4 ml) were added. The aqueous mixture was allowed to stand at room temperature for 1 day, and then extracted with methylene chloride. The organic layer was dried, and concentrated to afford 1.57 g of the desired product, 1-methyl-5-p-toluoylpyrrole-2-acetic acid. To the aqueous layer was further added dioxane (50 ml) and the mixture was allowed to stand for 2 days, and treated in the same manner as described above to afford an additional 400 mg of the desired product.

Total yield: 84%.

EXAMPLE 10—ADDUCT FORMATION-CATION EXCHANGE RESIN ADDED

To a solution of N-methylpyrrole (1.62 g, 20 mmol) in ether (10 ml) was added a solution of chloral (3.24 g, 22 mmol) in ether (10 ml). To this was added Amberlyst (160 mg) and the mixture was stirred under reflux for 18 hours. After cooling to room temperature and adding triethylamine (0.3 ml), the mixture was stirred for 5 minutes and filtered through a layer of Celite. The filtrate was concentrated under reduced pressure to afford the crude adduct 1-methyl-2-(2',2',2'-trichloro-1'-hydroxyethyl)pyrrole (4.68 g) as pale brown prisms.

EXAMPLE 11—CYANATION/BASIC HYDROLYSIS

1-Methyl-2-(2',2',2'-trichloro-1'-hydroxyethyl)pyrrole (1.14 g, 5 mmol), which was prepared by the procedure of Example 2, was dissolved in the solvent (15 ml) shown in the next table. After water (15 ml) and alkali metal cyanide (MCN: amount is shown in the table) were added to the solution, a solution of potassium hydroxide in water (10 ml) was added during a period of 6 hours under vigorous stirring at 45° C. After confirmation of the disappearance of starting chloral adduct (overnight), the reaction mixture was diluted with water (100 ml) and extracted twice with ethyl acetate. The combined organic extracts were washed with brine and dried over anhydrous magnesium sulfate. Most of the solvent was removed under reduced pressure and the residue was dissolved again in the 50 ml exact amount of ethyl acetate. A portion of the solution was taken up and treated with diazomethane dissolved in ether. After removal of the excess diazomethane under reduced pressure, trans-stilbene was added as the internal standard and the yield of methyl 5-cyano-1-methylpyrrole-2-acetate (theoretical yield; 5 mmol) was determined by GC (2% EGA column, 1 m, 160° C.).

TABLE
Preparation of 5-Cyano-1-Methylpyrrole-2-Acetic Acid

| Run | Solvent | MCN | MCN (mole ratio)$^a$ | KOH (mole ratio)$^a$ | Yield (%) |
|---|---|---|---|---|---|
| 1 | (HOCH$_2$)$_2$ | NaCN | 6 | 3 | 52.4 |
| 2 | MeOH | NaCN | 6 | 4 | 50.5 |
| 3 | MeOH | NaCN | 6 | 3 | 52.9 |
| 4 | MeOH | NaCN | 3 | 3 | 52.4 |
| 5$^b$ | MeOH | NaCN | 3 | 3 | 47.8 |
| 6 | MeOH | KCN | 3 | 3 | 52.9 |

$^a$The mole ratio to the starting 1-methyl-2-(2',2',2'-trichloro-1'-hydroxyethyl)pyrrole.
$^b$Aq. KOH solution was added during a period of 1.5 hours.

We claim:

1. A process for preparing 5-acyl-1-hydrocarbyl-pyrrole-2-acetic acids characterized by reacting a 5-cyano-1-hydrocarbylpyrrole-2-acetic acid with a Grignard compound and then hydrolyzing the resultant reaction product.

2. A process in accordance with claim 1 characterized by using more than 2 moles of the Grignard compound per mole of the 5-cyano-1-hydrocarbylpyrrole-2-acetic acid.

3. A process in accordance with claim 1 characterized in that the Grignard compound is an aryl Grignard compound.

4. A process in accordance with claim 1 characterized in that the 5-cyano-1-hydrocarbylpyrrole-2-acetic acid is 5-cyano-1-methylpyrrole-2-acetic acid.

5. A process in accordance with claim 1 characterized in that the Grignard compound is an aryl Grignard compound, in that the 5-cyano-1-hydrocarbylpyrrole-2-acetic acid is 5-cyano-1-methylpyrrole-2-acetic acid, and in that more than 2 moles of the aryl Grignard compound is used per mole of 5-cyano-1-methylpyrrole-2-acetic acid.

6. A process in accordance with any of claims 1–5 further characterized in that said 5-cyano-1-hydrocarbylpyrrole-2-acetic acid is prepared by reacting a 1-hydrocarbyl-2-(2',2',2'-trihalo-1'-hydroxyethyl)pyrrole with a cyanating reagent under basic conditions so that a cyano group is introduced into the pyrrole ring at the 5-position.

7. A process in accordance with claim 6 further characterized in that said 1-hydrocarbyl-2-(2',2',2'-trihalo-1'-hydroxyethyl)pyrrole is prepared by reacting a 1-hydrocarbylpyrrole with trichloroacetaldehyde.

8. A process in accordance with claim 6 further characterized in that said 1-hydrocarbyl-2-(2',2',2'-trihalo-1'-hydroxyethyl)pyrrole is prepared by reacting 1-methylpyrrole with trichloroacetaldehyde in the presence of a protonic acid catalyst added in the form of an organic acid or a cation exchange resin.

9. A process for preparing 5-cyano-1-hydrocarbylpyrrole-2-acetic acid characterized by reacting a 1-hydrocarbyl-2-(2',2',2'-trichloro-1'-hydroxyethyl)pyrrole with a cyanating agent under basic conditions so that a cyano group is introduced into the pyrrole ring at the 5-position.

10. A process in accordance with claim 9 further characterized in that the cyanating reagent is NaCN or KCN and in that sodium hydroxide or potassium hydroxide is also added to the reaction mixture.

11. A process in accordance with claim 10 further characterized by being performed in a mixed solvent composed of dimethyl sulfoxide and water or methanol and water.

12. A process in accordance with any of claims 9–11 further characterized in that said 1-hydrocarbyl-2-(2',2',2'-trichloro-1'-hydroxyethyl)pyrrole is prepared by reacting a 1-hydrocarbylpyrrole with trichloroacetaldehyde.

13. A process of preparing a 1-hydrocarbyl-2-(2',2',2'-trichloro-1'-hydroxyethyl)pyrrole characterized by reacting a 1-hydrocarbylpyrrole with trichloroacetaldehyde in the presence of a protonic acid added to the reaction mixture in the form of an organic acid or a cation exchange resin.

14. A process for preparing 5-aroyl-1-lower alkylpyrrole-2-acetic acids which comprises
  (i) reacting a 1-lower alkyl-2-(2',2',2'-trihalo-1'-hydroxyethyl)pyrrole with an inorganic cyanide under basic conditions so that a 5-cyano-1-lower alkylpyrrole-2-acetic acid is produced,
  (ii) reacting the 5-cyano-1-lower alkylpyrrole-2-acetic acid with an aryl Grignard compound so that the aryl Grignard compound interacts with the cyano group on the pyrrole ring to form a ketimine salt, and then
  (iii) hydrolyzing the resultant product.

15. A process in accordance with claim 14 further characterized in that said 1-lower alkyl-2-(2',2',2'-trihalo-1'-hydroxyethyl)pyrrole is 1-methyl-2-(2',2',2'-trichloro-1'-hydroxyethyl)pyrrole, in that the inorganic cyanide is NaCN or KCN, and in that sodium hydroxide or potassium hydroxide is also added to the reaction mixture of (i).

16. A process in accordance with claim 14 or claim 15 further characterized in that the aryl Grignard compound is a p-tolyl Grignard compound.

17. A process in accordance with claim 13 wherein said 1-hydrocarbylpyrrole is further characterized in that the hydrocarbyl group on the nitrogen atom is lower alkyl, phenyl, benzyl, or cyclohexyl and in that, optionally, the 3- and/or 4-positions of the pyrrole ring are alkyl-substituted.

18. A process of preparing a 1-hydrocarbyl-2-(2',2',2'-trichloro-1'-hydroxyethyl)pyrrole characterized by reacting a 1-hydrocarbylpyrrole with trichloroacetaldehyde in the presence of a protonic acid.

19. 5-Cyano-1-methylpyrrole-2-acetic acid.

20. A 5-cyano-1-hydrocarbylpyrrole-2-acetic acid in which the hydrocarbyl group on the nitrogen atom is lower alkyl, phenyl, benzyl, or cyclohexyl.

21. A 5-cyano-1-hydrocarbylpyrrole-2-acetic acid in which the hydrocarbyl group on the nitrogen atom is lower alkyl, phenyl, benzyl, or cyclohexyl, and in which the 3- and/or 4-positions of the pyrrole ring are substituted by an innocuous alkyl group.

* * * * *